(12) United States Patent
Surti

(10) Patent No.: US 9,259,222 B2
(45) Date of Patent: *Feb. 16, 2016

(54) MEDICAL STAPLER

(71) Applicant: Cook Medical Technologies LLC, Bloomington, IN (US)

(72) Inventor: Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 511 days.

This patent is subject to a terminal disclaimer.

(21) Appl. No.: 13/688,453

(22) Filed: Nov. 29, 2012

(65) Prior Publication Data

US 2013/0087598 A1   Apr. 11, 2013

Related U.S. Application Data

(63) Continuation of application No. 11/448,494, filed on Jun. 7, 2006, now Pat. No. 8,342,376.

(51) Int. Cl.
| | |
|---|---|
| *A61B 17/068* | (2006.01) |
| *A61B 17/064* | (2006.01) |
| *A61B 17/00* | (2006.01) |
| *A61B 17/08* | (2006.01) |

(52) U.S. Cl.
CPC ........... *A61B 17/0682* (2013.01); *A61B 17/064* (2013.01); *A61B 17/0644* (2013.01); *A61B 2017/00867* (2013.01); *A61B 2017/081* (2013.01)

(58) Field of Classification Search
CPC ............................ A61B 17/068; A61B 17/072
USPC ................. 227/175.1, 176.1, 180.1; 606/151
See application file for complete search history.

(56) References Cited

U.S. PATENT DOCUMENTS

| | | |
|---|---|---|
| 2,797,275 A | 6/1957 | Seeger |
| 4,485,816 A | 12/1984 | Krumme |
| 4,550,870 A | 11/1985 | Krumme et al. |
| 4,719,917 A | 1/1988 | Barrows et al. |
| 4,787,899 A | 11/1988 | Lazarus |

(Continued)

FOREIGN PATENT DOCUMENTS

| | | |
|---|---|---|
| EP | 1 016 378 A1 | 7/2000 |
| EP | 1 199 038 A2 | 4/2002 |

(Continued)

OTHER PUBLICATIONS

McDonald Schetky, L.; "Shape Memory Alloys;" Scientific American, vol. 281; pp. 74-82; Nov. 1979.

(Continued)

*Primary Examiner* — Nathaniel Chukwurah
(74) *Attorney, Agent, or Firm* — Brinks Gilson & Lione

(57) ABSTRACT

A medical device for delivering a staple formed from a shape memory material is disclosed. The staple includes a first tine and a second tine connected by a bridge. The staple may be disposed within the medical device in an open position. The medical device is configured to sequentially deliver the first tine and the second tine, respectively, to opposing body tissues. Upon warming up to a temperature at or above a transformation temperature of the shape memory material, the staple may assume a closed position, thus drawing together opposing body tissues and closing an incision.

20 Claims, 6 Drawing Sheets

(56) References Cited

U.S. PATENT DOCUMENTS

| | | |
|---|---|---|
| 5,002,563 A | 3/1991 | Pyka et al. |
| 5,067,957 A | 11/1991 | Jervis |
| 5,190,546 A | 3/1993 | Jervis |
| 5,219,358 A | 6/1993 | Bendel et al. |
| 5,258,009 A | 11/1993 | Conners |
| 5,342,395 A | 8/1994 | Jarrett et al. |
| 5,342,396 A | 8/1994 | Cook |
| 5,350,400 A | 9/1994 | Esposito et al. |
| 5,395,381 A | 3/1995 | Green et al. |
| 5,397,345 A | 3/1995 | Lazarus |
| 5,441,509 A | 8/1995 | Vidal et al. |
| 5,597,378 A | 1/1997 | Jervis |
| 5,662,700 A | 9/1997 | Lazarus |
| 5,673,840 A | 10/1997 | Schulze et al. |
| 5,817,113 A | 10/1998 | Gifford, III et al. |
| 5,906,573 A | 5/1999 | Aretz |
| 6,017,364 A | 1/2000 | Lazarus |
| 6,030,413 A | 2/2000 | Lazarus |
| 6,113,611 A | 9/2000 | Allen et al. |
| 6,119,913 A | 9/2000 | Adams et al. |
| 6,193,733 B1 | 2/2001 | Adams |
| 6,198,974 B1 | 3/2001 | Webster, Jr. |
| 6,293,949 B1 | 9/2001 | Justis et al. |
| 6,306,141 B1 | 10/2001 | Jervis |
| 6,329,069 B1 | 12/2001 | Azizi et al. |
| 6,416,535 B1 | 7/2002 | Lazarus |
| 6,461,453 B1 | 10/2002 | Abrams et al. |
| 6,610,085 B1 | 8/2003 | Lazarus |
| 6,638,297 B1 | 10/2003 | Huitema |
| 6,685,708 B2 | 2/2004 | Monassevitch et al. |
| 6,702,844 B1 | 3/2004 | Lazarus |
| 6,761,719 B2 | 7/2004 | Justis et al. |
| 2002/0065524 A1* | 5/2002 | Miller et al. .............. 606/139 |
| 2005/0021054 A1 | 1/2005 | Ainsworth et al. |
| 2005/0080454 A1 | 4/2005 | Drews et al. |
| 2005/0283190 A1 | 12/2005 | Huitema et al. |

FOREIGN PATENT DOCUMENTS

| | | |
|---|---|---|
| EP | 1 100 381 B1 | 8/2005 |
| WO | WO 00/07506 A2 | 2/2000 |

OTHER PUBLICATIONS

International Search Report dated Oct. 23, 2006 for International Application No. PCT/US2006/022158.

International Preliminary Report on Patentability dated Aug. 6, 2007 for International Application No. PCT/US2006/022158.

* cited by examiner

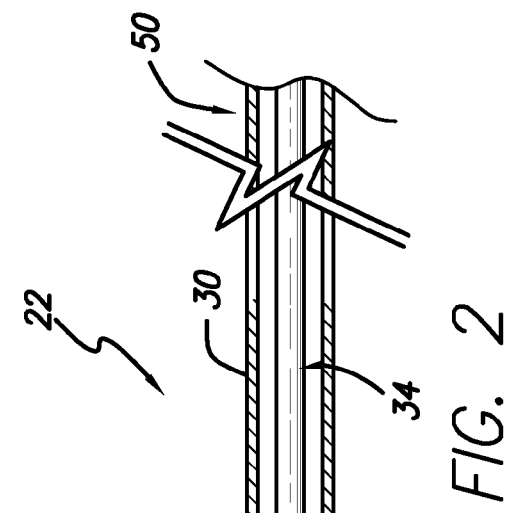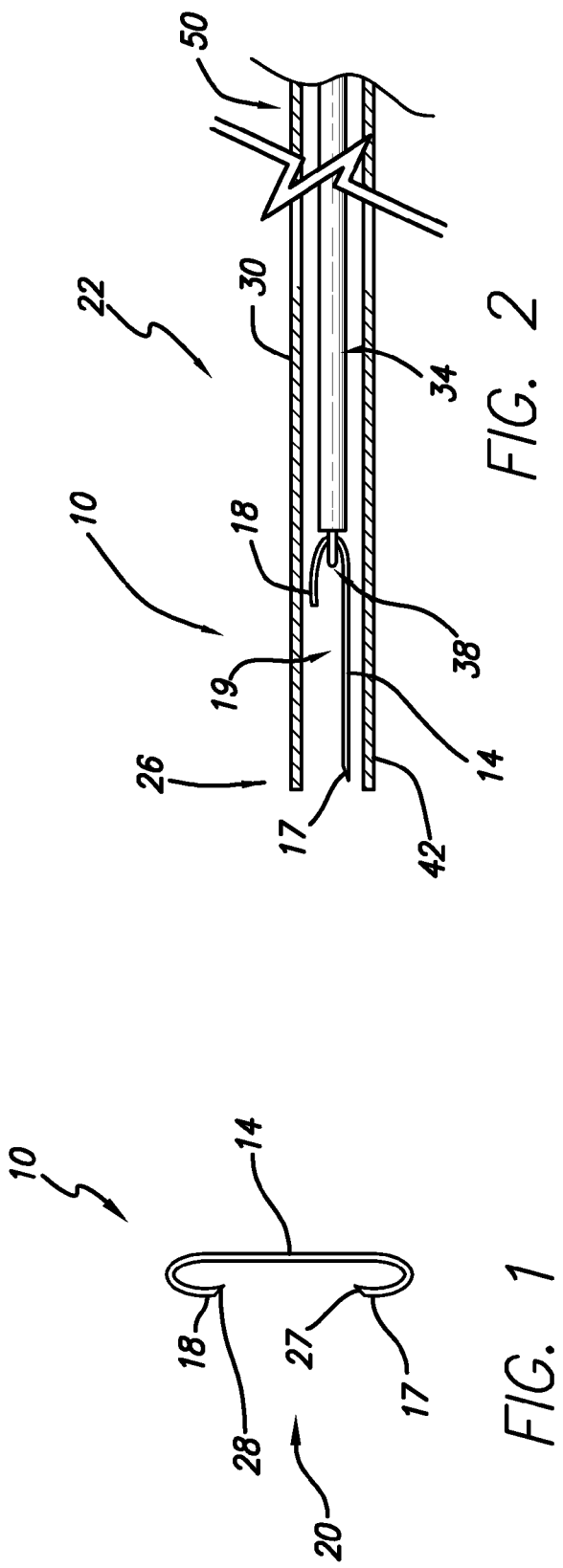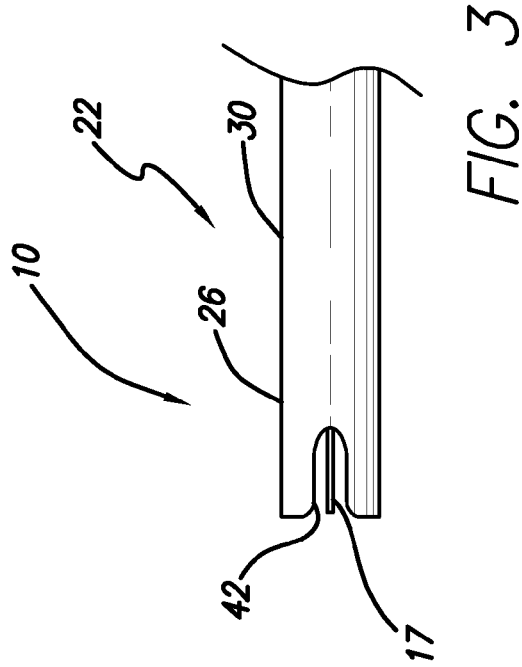

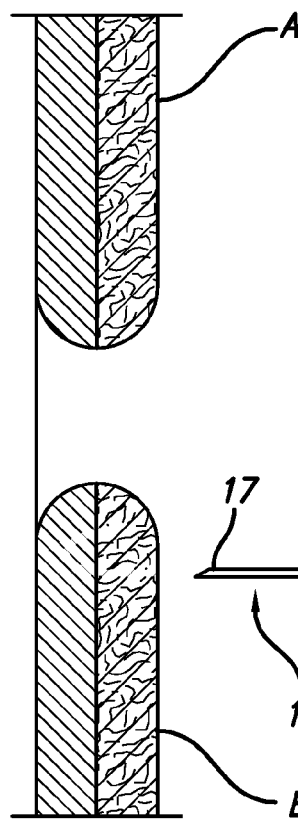
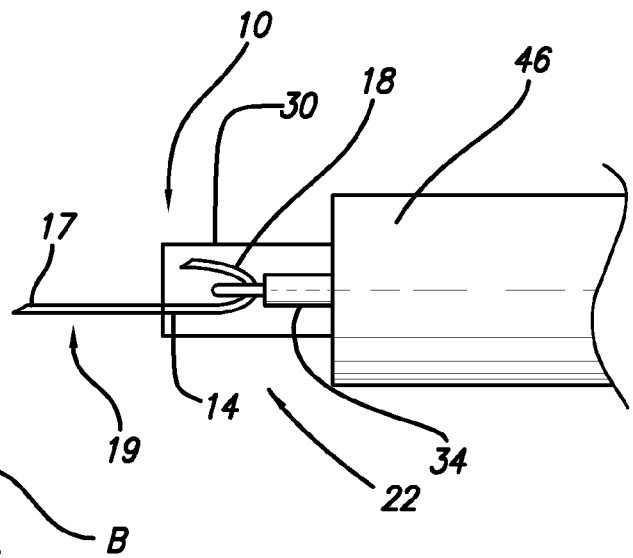
FIG. 4
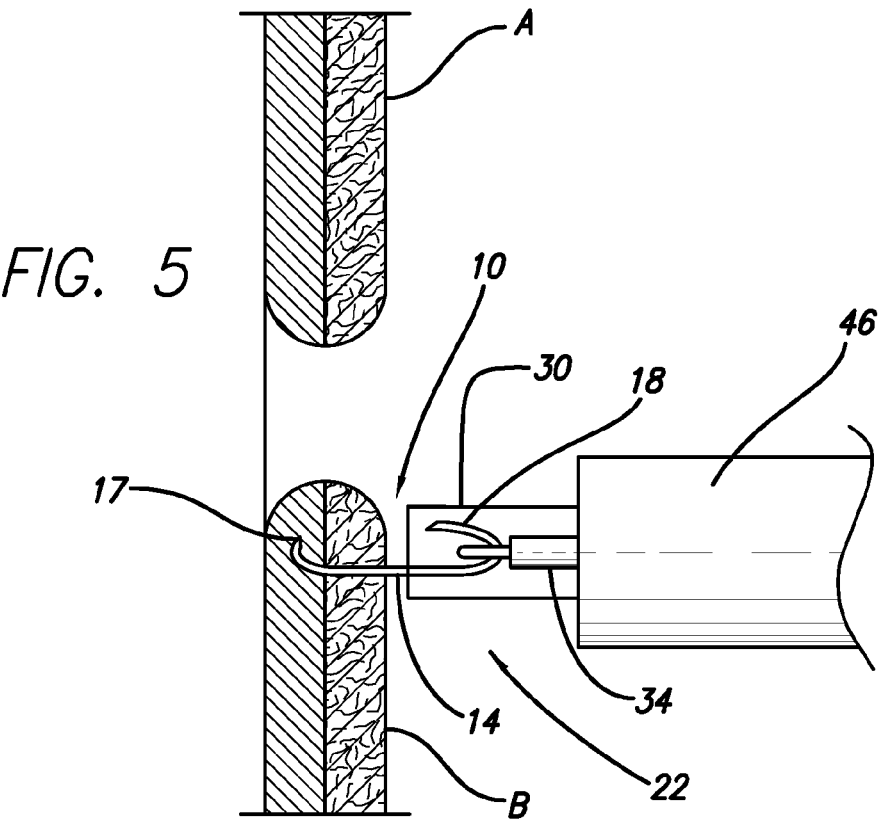
FIG. 5

MEDICAL STAPLER

RELATED APPLICATIONS

This application is a continuation of U.S. application Ser. No. 11/448,494, filed Jun. 7, 2006 that claims the benefit of U.S. Provisional Application No. 60/689,589, filed Jun. 10, 2005, which are incorporated by reference in their entirety.

TECHNICAL FIELD

This disclosure generally relates to medical devices, and particularly to surgical staples and devices for delivering surgical staples.

BACKGROUND

Surgical stapling is commonly used to close surgical incisions. Surgical stapling benefits the patient by reducing the amount of time the patient is under anesthesia. It also benefits physicians by eliminating much of the time and energy that was previously spent suturing surgical incisions with traditional needle and silk, polymer, or gut thread. As a result, surgical stapling has become the procedure of choice for incision closure, especially when confronting large incisions or wounds.

Conventional staples used in surgical stapling initially were formed from stainless steel. However, properly deploying stainless steel staples proved difficult because of the substantial amount of force required to deform stainless steel staples into a closed position. A great deal of innovation was thus directed to surgical staplers. Despite this effort, surgical staplers continue to suffer from one or more of the following drawbacks. Surgical staplers are relatively heavy and bulky; they are expensive because of their complex inner workings; they often obstruct the target location for the staple; and each stapler is intended for a narrow range of procedures.

As a result of their unique characteristics, shape memory alloys ("SMAs") have become viable alternatives to stainless steel. Shape memory materials are capable of returning to a previously defined shape and size when subjected to an appropriate thermal treatment. For example, a shape memory material having an initial configuration above a first transformation temperature may be cooled to below a second transformation temperature and then deformed to take on a different configuration. Then, upon heating above the first transformation temperature, the material may "remember" and spontaneously recover the initial configuration. The basis for this behavior is a substantially reversible phase transformation that occurs when the temperature of the material moves below and above its transformation temperatures. Using surgical staples formed from SMAs may reduce or eliminate the need to apply a substantial deforming force to fasten the staples. A shape memory surgical staple is described in U.S. Pat. No. 4,485,816, to Krumme, entitled "SHAPE-MEMORY SURGICAL STAPLE APPARATUS AND METHOD FOR USE IN SURGICAL STAPLING," which is incorporated herein by reference in its entirety.

Despite the significant advance of using SMA surgical staples instead of stainless steel surgical staples, the staplers used to deliver SMA surgical staples suffer from one or more of the following drawbacks. First, such staplers are unsuitable for use in endoscopic procedures. That is, such staplers are not deliverable through the working channel of an endoscope. Accordingly, endoscopically (or laparascopically) created incisions cannot be closed with traditional SMA staplers. Second, these staplers require that both tines of a staple be simultaneously inserted into the opposing tissues of an incision. This requires that a physician use one hand to approximate both opposing tissues of an incision and another hand to simultaneously insert the tines of the staple into the respective opposing sides. This can be particularly limiting during endoscopic procedures in which the physician needs one hand to operate the endoscope. Moreover, since both tines enter the opposing sides of the tissue simultaneously, the tines cannot be used to gather and approximate the opposing tissues. Accordingly, there is a need for a stapler and an SMA staple that resolves or improves upon any of these drawbacks.

BRIEF SUMMARY

A medical device is disclosed herein that may provide advantages over medical staplers known in the art. The medical device of the present disclosure may be suitable for use in endoscopic procedures, for example, and may allow a physician to approximate opposing tissues with one hand while operating an endoscope with the other.

According to one aspect of the present invention, the medical device includes an elongate shaft having a working lumen. A staple is disposed in the working lumen in an open position. The staple includes a first tine and a second tine connected by a bridge portion. The staple comprises a shape memory material and is configured to transition from the open position to a closed position at or above a transformation temperature of the shape memory material. The first tine is disposed distal of the second tine in the working lumen.

According to another aspect of the present invention, the medical device includes a staple formed from a shape memory material. The staple has an open position and a closed position. The medical device also includes an elongate shaft having a working lumen extending at least partially therethrough. The working lumen is adapted for receiving the staple in the open position. The medical device also includes a control member extending along the lumen. The control member is adapted for delivery of the staple to a body tissue. The staple assumes the closed position when disposed in the body tissue.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

Embodiments of the present invention will now be described by way of example with reference to the accompanying drawings, in which:

FIG. 1 illustrates a side view of a surgical staple according to one embodiment of the present invention;

FIG. 2 illustrates a side view of a stapler with a cut-away distal portion according to one embodiment of the present invention;

FIG. 3 illustrates a partial side view of a stapler, according to one embodiment of the present invention;

FIG. 4 illustrates a partial side view of a stapler according to one embodiment of the present invention and a surgical incision;

FIG. 5 illustrates a partial side view of a stapler according to one embodiment of the present invention and a staple deployed through one side of a surgical incision;

DETAILED DESCRIPTION OF THE PREFERRED EMBODIMENTS

Figure 6:
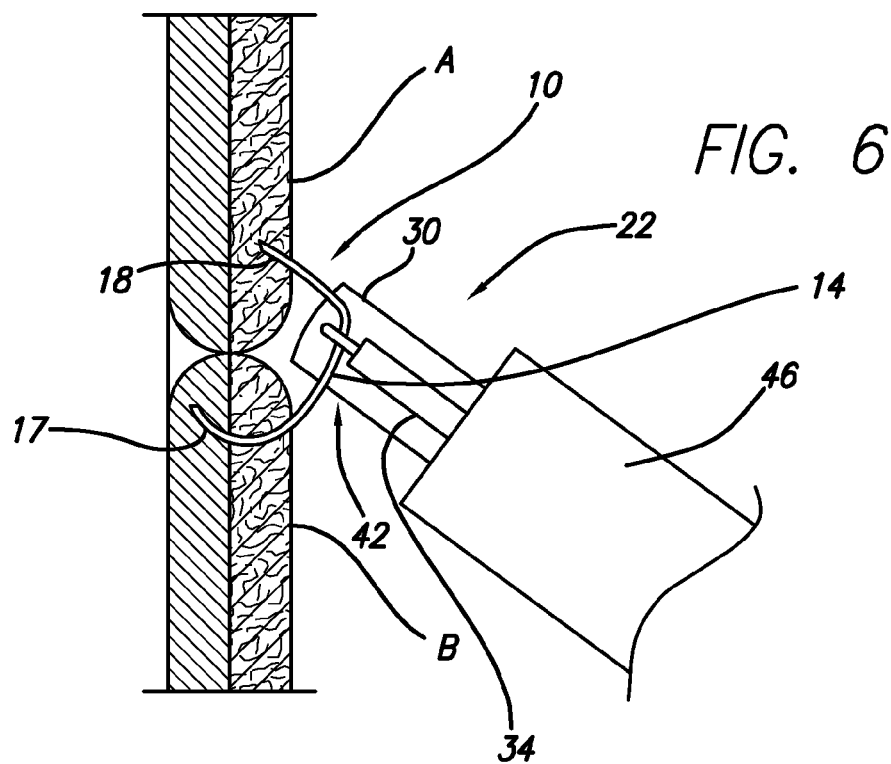
FIG. 6 illustrates a partial side view of a stapler according to one embodiment of the present invention and a staple deployed through one tissue path.
Figure 7:
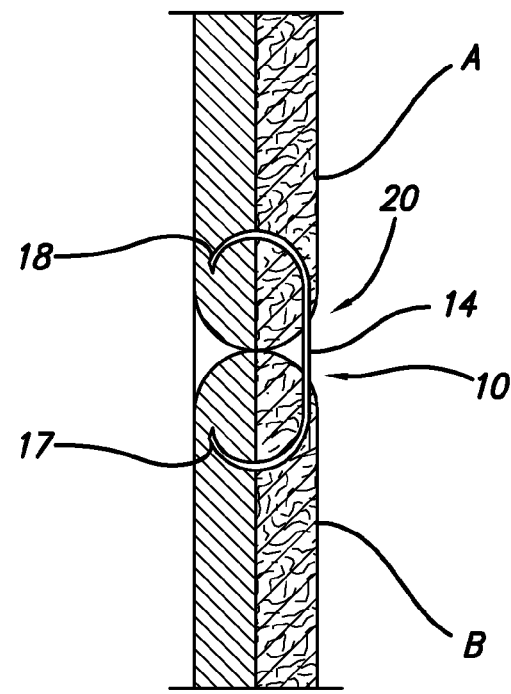
FIG. 7 illustrates a cross-sectional side view of a staple securing opposing sides of a tissue.

The invention is described with reference to the drawings in which like elements are referred to by like numerals. The relationship and functioning of the various elements of this invention are better understood by the following detailed description. However, the embodiments of this invention as described below are by way of example only, and the invention is not limited to the embodiments illustrated in the drawings. It should also be understood that the drawings are not to scale and in certain instances details have been omitted which are not necessary for an understanding of the present invention, such as conventional details of fabrication and assembly.

Referring now to the Figures, there is shown in FIG. 1 a staple 10 having a bridge 14 connecting a first tine 17 and a second tine 18. The first and second tines 17, 18 may include first and second ends 27, 28 that are adapted to penetrate tissue. The first and second ends 27, 28 may facilitate entry of the first and second tines 17, 18 into the tissue to be approximated. By way of non-limiting example, the ends 27, 28 may be straight or angled, and may include a sharpened or beveled point. The ends 27, 28 may also be adapted to anchor the staple in place after the ends 27, 28 have entered the tissue. For example, the ends 27, 28 may include barbs. The staple comprises a shape memory material.

As illustrated in FIG. 1, the staple 10 is in a closed position 20. In the closed position 20, the first tine 17 and the second tine 18 are bent toward each other. In an open position 19 of the staple 10, as illustrated for example in FIG. 2, at least one of the first tine 17 and the second tine 18 extends generally along a line of the bridge 14. In other words, at least one of the first tine 17 and the second tine 18 is not bent toward the other in the open position 19. When the staple 10 is in the closed position 20, the shape memory material may comprise a high temperature phase. According to one embodiment, the high temperature phase is austenite. When the staple 10 is in the open position 19, the shape memory material may comprise a low temperature phase. According to one embodiment, the low temperature phase is martensite.

FIG. 2 further illustrates a stapler 22 that may be used to insert the staple 10. The stapler 22 may be formed, for example, from an elongate shaft (e.g., a catheter 30) having a proximal end 50 and a distal end 26. As shown in FIG. 2, the distal end 26 may be configured to deliver the staple 10, which is illustrated in an open position 19. In the open position 19 within the stapler 22, the staple is disposed with an end of the first tine 17 distal of the second tine 18. In general, as will be explained in greater detail below, the catheter can be used through the working channel of an endoscope to approximate the opposing portions of a tissue using the first and second tines 17 and 18. Referring to FIGS. 4-7, once the first tine 17 penetrates a body tissue, the body tissue temperature causes the first tine 17 of the staple 10 to warm up and assume a closed configuration. The stapler 22 may then be used to pull the tissue with the first tine 17 inserted therein into close apposition with a second tissue for insertion of the second tine 18. The second tine 18 may then be inserted into the body tissue and assume a closed configuration upon warming up, thus drawing together the body tissue and closing the incision. At this point, the staple 10 is in the closed position 20.

Figure 8:
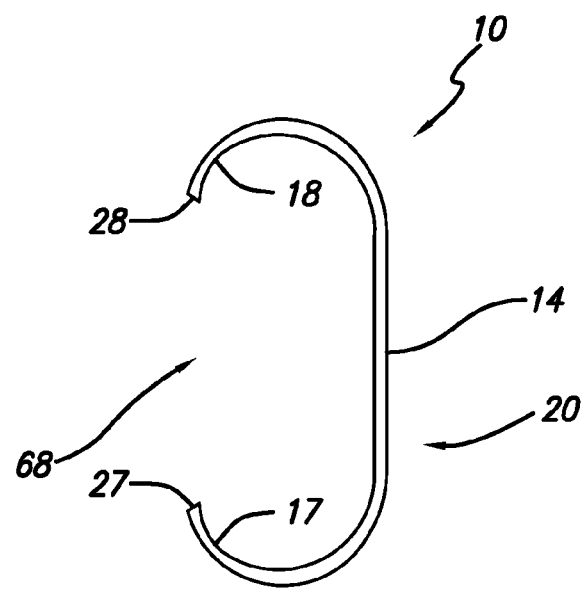
FIG. 8 illustrates a side view of a surgical staple according to one embodiment of the present invention.
Figure 9:
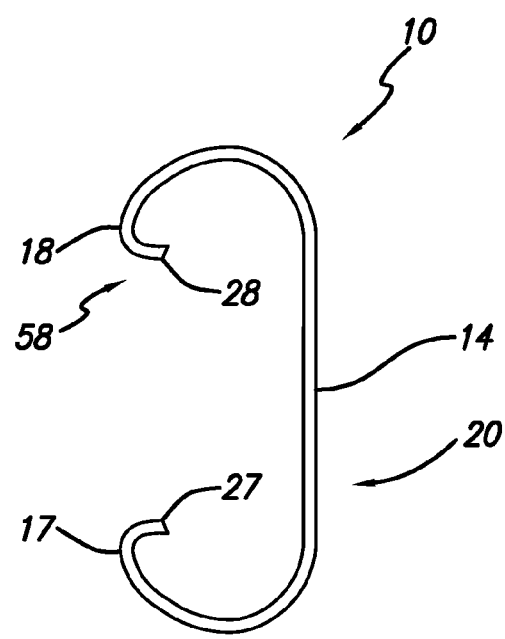
FIG. 9 illustrates a side view of a surgical staple according to another embodiment of the present invention.

According to one embodiment, when the staple 10 is in the closed position 20, the end 27 of the first tine 17 may generally face the end 28 of the second tine 18, as shown, for example, in the configuration 68 illustrated in FIG. 8. According to another embodiment, when the staple 10 is in the closed position 20, the end 27 of the first tine 17 and the end 28 of the second tine 18 may generally face the bridge portion 14, as shown, for example, in the configuration 58 illustrated in FIG. 9.

Figures 10A, 10B, 10C:
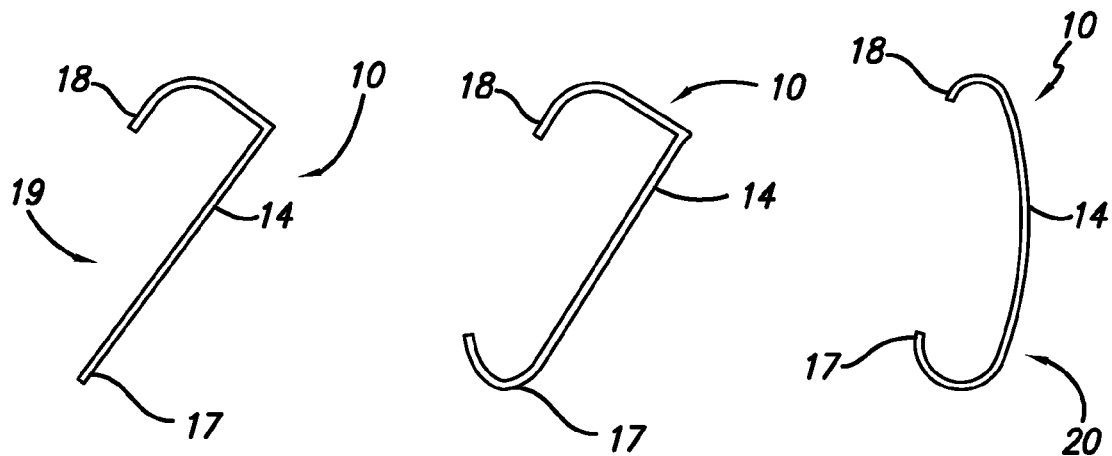
FIGS. 10A-10C illustrate the transition of a surgical staple of the present invention from an open position to a closed position.
Figures 11A, 11B, 11C:
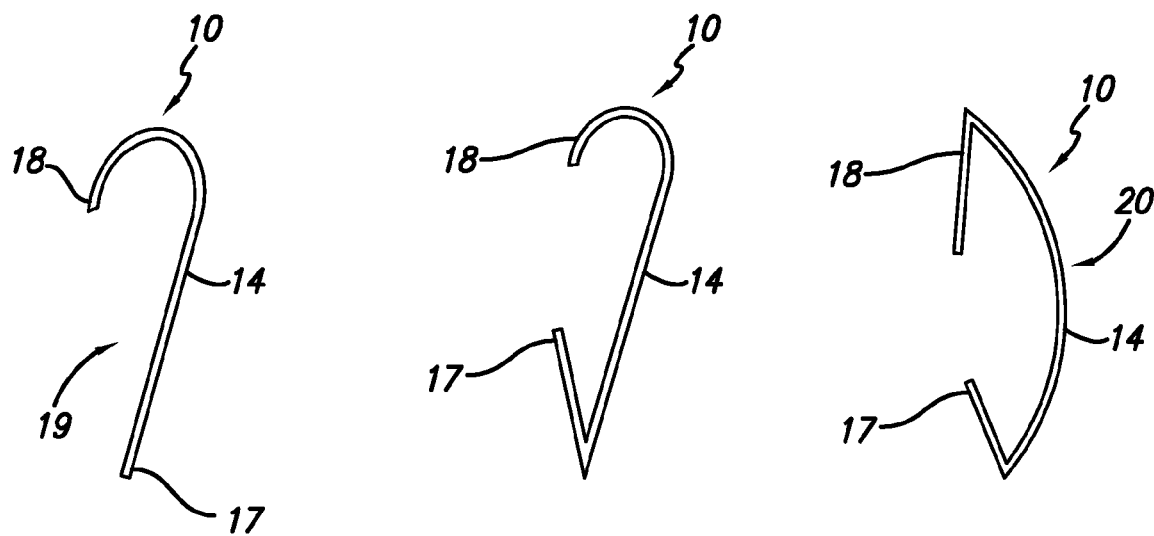
FIGS. 11A-11C illustrate the transition of an alternative embodiment of a surgical staple from an open position to a closed position.

In the open position 19, the staple 10 can be provided in a variety of shapes that fit within the lumen of a catheter and that allow the staple to be deployed from the distal end of the catheter. In the embodiment shown in FIG. 2, the staple 10 includes a linear (straight) bridge 14 between a first tine 17 and a second tine 18. According to this embodiment, the first tine 17 is generally straight and extends along the line of the bridge 14, and the second tine 18 is bent. Specifically, the second tine 18 is curved. Alternatively, the second tine 18 may be angled. For the purposes of this disclosure, "bent" is used to refer to a curved or an angled configuration. The staple 10 may also be provided in the open position 19 with both the first and second tines 17 and 18 extending along the line of the bridge 14. In another embodiment, the first tine 17 may be bent (curved or angled), and the second tine 18 may extend along the line of the bridge 14. In some embodiments, the bridge 14 may be bent (angled or curved) in the open position 19 to facilitate insertion of the second tine 18 into the second tissue after the first tine 17 has transitioned to its closed position, as illustrated, for example, in FIGS. 10A-10C. In the open position 19, the bent bridge 14 may be combined with two straight first and second tines 17, 18, with a straight first tine 17 and a curved or angled second tine 18, or with a straight second tine 18 and a curved or angled first tine 17.

Preferably, in the closed position 20, both the first and second tines 17, 18 may be bent toward each other so as to approximate an incision. The first and second tines 17 and 18 may have different configurations in the closed position 20 as well as in the open position 19 (as described above). For example, in some embodiments, the first tine 17 may be curved and the second tine 18 may be angled in the closed position 20. Alternatively, the first tine 17 may be angled and the second tine may be curved in the closed position 20. The bridge 14 may be straight, angled or curved in the closed position 20.

Figure 12:
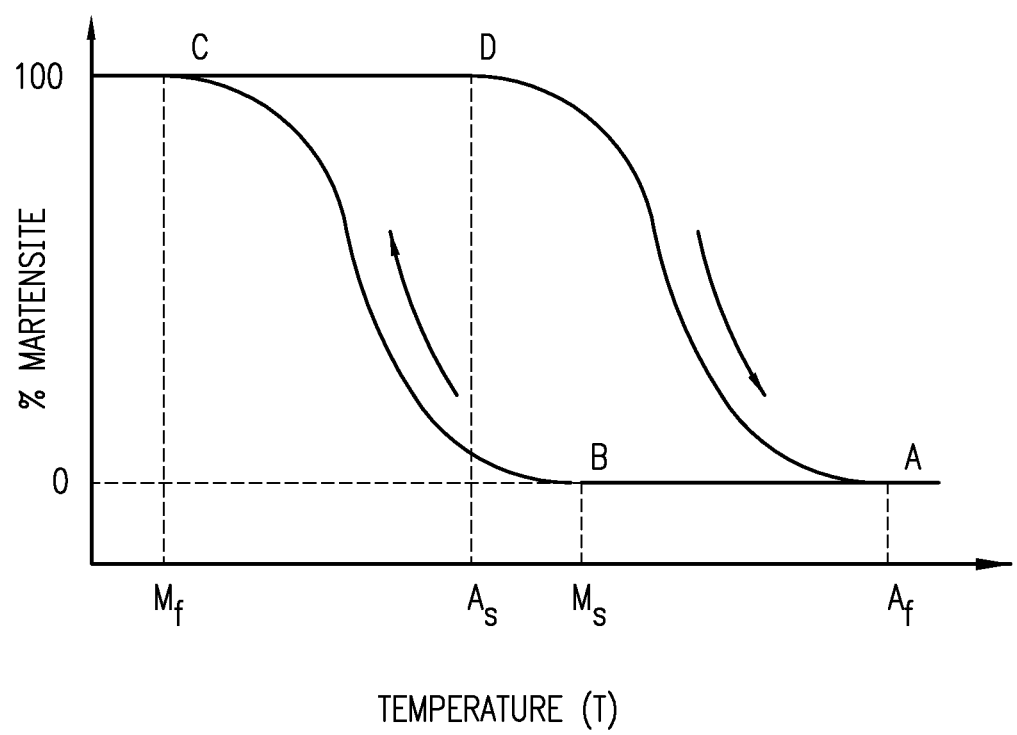
FIG. 12 is a typical transformation temperature curve for shape memory alloys.

The staple 10 may be formed from a shape memory material. A shape memory alloy including nickel and titanium, such as Nitinol, may be used. Shape memory alloys may undergo a reversible transformation between an austenitic phase and a martensitic phase at certain predetermined temperatures. The behavior of shape memory alloys depends on their transformation temperatures. FIG. 12 shows a typical transformation temperature curve for a shape memory alloy. The y-axis indicates the percentage of the martensitic phase present in the material, and the x-axis indicates temperature. At point A, the shape memory material is at a temperature $A_f$ and the structure is fully austenitic. No martensite is present in the material. Following the curve to point B, the shape memory material is cooled to a temperature of $M_s$, at which point the transformation to the martensitic phase begins. Further cooling leads to an increase in the percentage of martensite in the material, ultimately reaching 100% at a temperature of $M_f$. At this point (C), the shape memory material is fully martensitic. No austenite is present in the material. To reverse the phase transformation and return to a fully austenitic structure, the temperature of the material must be increased. Following the curve to point D, the shape memory material may be warmed to a temperature of $A_s$, at which point the material begins to transform to the austentic phase. Upon further heating, the percentage of the martensitic phase in the material decreases as the transformation to austenite progresses. Ultimately, at a temperature of $A_f$ or above, the material has completed the return transformation to the austenitic phase.

In practice, differential scanning calorimetry techniques known in the art may be used to identify the transformation temperatures of a particular shape memory material. The transformation temperatures may be affected by the alloy composition and the processing history of the material. In developing the correct alloy composition, biological temperature compatibility may be considered in order to select suitable transformation temperatures. For example, shape memory materials can be prepared such that $A_f$ is slightly lower than or equal to body temperature. Such materials will remember and return to their initial configuration when they come into contact with body tissue or are otherwise warmed up to about body temperature. It may be desirable to select a shape memory material for the staple 10 of the present disclosure having a value of $A_f$ which is slightly lower than or about equal to body temperature (37° C.). For example, $A_f$ may be in the range from about 32° C. to about 40° C. According to another embodiment, $A_f$ may be in the range from about 36° C. to about 38° C. Alternatively, shape memory materials having higher or lower values of $A_f$ may be used for the staple 10. For example, it may be desirable to have $A_f$ in the range of from about 40° C. to about 60° C., e.g., 50° C. According to another embodiment, $A_f$ may be less than 32° C.

Depending on the precise transformation temperatures (e.g., $A_f$) of the shape memory alloy used for the staple 10, the staple 10 may require heating or cooling from an external source during delivery within the body. For example, according to some embodiments, cooling may be desirable to prevent premature transformation to the austenitic phase and, consequently, the closed position 20. Such cooling may be carried out by, for example, periodically or continuously flushing the catheter 30 with a cool saline solution. Alternatively, the staple 10 may require heating from an external source in order to facilitate transformation to the austenitic phase and, consequently, the closed position 20. Such heating may be carried out by, for example, periodically or continuously flushing the catheter 30 with a warm saline solution. In either of these situations, the staple 10 and the heating or cooling means (e.g., saline solution) may be maintained at temperatures that are compatible with the surrounding body tissue.

In some embodiments, the shape memory material may be formed from a nickel-titanium composition (e.g., Nitinol) known in the art. The shape memory material may alternatively be formed from a composition consisting essentially of about 30 to about 52 percent titanium, up to 10 percent of one or more additional ternary alloying elements, and the balance nickel. Such ternary alloying elements may be selected from the group consisting of palladium, platinum, chromium, iron, cobalt, vanadium, manganese, boron, copper, aluminum, tungsten, tantalum, and zirconium. In particular, the ternary element may optionally be up to 10 percent each of iron, cobalt, platinum, palladium, or chromium, and up to about 10 percent copper and vanadium. As used herein, all references to percent composition are atomic percent unless otherwise noted. Other shape memory materials may also be utilized, such as, but not limited to, irradiated memory polymers such as autocrosslinkable high density polyethylene (HDPEX). Shape memory alloys are known in the art and are discussed in, for example, "Shape Memory Alloys," *Scientific American*, Vol. 281, pp. 74-82 (November 1979).

Briefly, the staple 10 may be formed into any desired closed position 20 while the shape memory material is in the austenitic phase by, for example, shaping on a mandrel. Then, the staple 10 may be provided in the open position 19 for being received by the lumen of the catheter 30 for delivery to body tissue. Generally, providing the staple 10 in the open position 19 involves cooling the staple 10 to a temperature at or below $M_f$ of the shape memory material. This cooling effects a complete transformation of the shape memory material from the high temperature phase (austenite) to the low temperature phase (martensite) (see FIG. 12). Once the staple 10 has a fully martensitic structure, the staple 10 may be deformed into the open position 19 from the closed position 20. Elastic (recoverable) strains of up to about 8% may be obtainable from nickel-titanium shape memory alloys.

After deformation, if the temperature of the staple 10 is kept below about $A_s$, the staple may remain in the open position 19. If the temperature of the staple 10 is raised to $A_f$ or above, then the staple 10 may completely transform to the austenitic phase and remember (return to) its closed position 20. At temperatures below $A_f$ and at or above $A_s$, the staple may partially transform to the austenitic phase and exhibit some change in its configuration without completely transforming to the closed position 20. In other words, the staple may be partly martensitic and partly austenitic within this temperature range. It may be desirable for the staple to be delivered to the body tissue at a temperature within this range (below $A_f$ but at or above $A_s$) in order to exploit the higher rigidity of the austenitic phase compared to the more deformable martensitic phase. The enhanced rigidity may be useful for the initial penetration of body tissue by the ends 27, 28 of the staple 10, for example. Alternatively, it may be advantageous in some embodiments to maintain the staple 10 at a temperature below $A_s$ during delivery.

The staple 10 may transition from the open position 19 in the catheter 30 to the closed position 20 in a tissue in a stepwise fashion, wherein the first tine 17 transitions to the austenitic phase prior to the second tine 18. FIGS. 4-7, 10A-10C and 11A-11C show exemplary staples transitioning from the open position 19 to the closed position 20. In the open position 19, the first tine 17 of the staple 10 is disposed distal of the second tine 18 within the lumen of the catheter 30 (see FIG. 4). Upon being heated to a temperature of $A_f$ or higher, the first tine 17 may transition to its final (closed) configuration, as shown for example in FIGS. 5, 10B, and 11B. The heating may occur as the first tine 18 is being inserted into body tissue, for example, or by some other means. The second tine 18 may remain in its initial configuration after the first tine 17 has transitioned to the final configuration. The second tine 18 may then be heated to a temperature of $A_f$ or higher upon entry into the body tissue (or by other means) and transition to its final (closed) configuration. Consequently, the staple 10 reaches the closed position 20, shown in FIGS. 7, 10C, and 11C.

Referring now to FIGS. 2-3, the delivery catheter 30 includes a proximal end 50 and a distal end 26. The proximal end 50 is used to control the catheter 30 and to actuate the stapler 22. Operation of the delivery catheter 30 takes place via the proximal end 50 (FIG. 2), which is provided with a conventional handle (not shown). As will become apparent to a person of ordinary skill, a wide variety of handle mechanisms could be used with the disclosed medical stapler. For example, the handle can be a thumb ring, a scissors-type handle, a pin vise, or any other conventional handle suitable for moving a sheath relative to a control wire. In general, the handle is used to actuate the control wire, which in turn controls the stem movement. That is, the handle is connected to and causes the control wire to move relative to the catheter 30 or vice versa.

As illustrated in FIGS. 2-3, the stapler 22 has a control wire 34 that extends to the distal end 26 of the catheter 30. The control wire 34 can be formed from a rigid material such as stainless steel or plastic. The distal end of the control wire 34 is provided with a hook 38. The hook 38 is configured to catch and clasp (i.e., secure) the staple 10 during delivery and insertion, thereby preventing the staple 10 from inadvertently sliding out of the stapler 22. The distal end 26 further includes a slot 42 (FIG. 3), which allows the staple to rotate during insertion as described in greater detail below. Any device known to one of skill in the art may be used to manipulate the staple 10 for insertion into the tissue.

FIGS. 4-6 illustrate a method of approximating opposing tissues with the staple 10 and the stapler 22. As shown in FIG. 4, an endoscope 46 is navigated to the site of opposing tissues A and B. Once the endoscope 46 is adjacent opposing tissues A and B, the physician actuates the catheter handle to move the control wire 34 distally, i.e., toward opposing tissues A and B. Stapler 22 is then moved toward tissue B, as shown in FIG. 5, so that the first tine 17 penetrates or pierces the tissue. When the first tine 17 of the staple 10 penetrates tissue B, the exposure to body temperature causes the first tine 17 of the staple to assume its closed configuration. After the first tine 17 assumes its closed position, the physician can move the distal end of the stapler 22 towards tissue A using the first tine 17 in tissue B to pull tissue B towards tissue A. As illustrated in FIG. 6, a portion of the staple 10 may extend through the slot 42 as the tissue B is approximated with tissue A allowing the staple 10 to be rotated after the second tine 18 is inserted into tissue B. At this point in the procedure, the physician can insert the second tine 18 into tissue A. Once the second tine 18 is heated by exposure to body temperature, the second tine 18 assumes its closed configuration, and the control wire 34 can be moved distally and laterally relative to the staple 10 to disengage the hook 38 from the staple 10. When the temperature of the staple 10 reaches or exceeds $A_f$, the staple 10 assumes the closed position 20 illustrated in FIG. 7, thereby approximating opposing tissues A and B.

Any other undisclosed or incidental details of the construction or composition of the various elements of the disclosed embodiment of the present invention are not believed to be critical to the achievement of the advantages of the present invention, so long as the elements possess the attributes needed for them to perform as disclosed. Certainly, one skilled in the medical arts would be able to conceive of a wide variety of staple shapes and delivery system configurations and successful combinations thereof. The selection of these and other details of construction are believed to be well within the ability of one of even rudimentary skills in this area, in view of the present disclosure. Illustrative embodiments of the present invention have been described in considerable detail for the purpose of disclosing a practical, operative structure whereby the invention may be practiced advantageously. The designs described herein are intended to be exemplary only. The novel characteristics of the invention may be incorporated in other structural forms without departing from the spirit and scope of the invention. The invention encompasses embodiments both comprising and consisting of the elements described with reference to the illustrative embodiments. Unless otherwise indicated, all ordinary words and terms used herein shall take their customary meaning as defined in *The New Shorter Oxford English Dictionary*, 1993 edition. All technical terms shall take on their customary meaning as established by the appropriate technical discipline utilized by those normally skilled in that particular art area. All medical terms shall take their meaning as defined by *Stedman's Medical Dictionary*, 27th edition.

The invention claimed is:

1. A medical device, comprising:
   an elongate shaft having a working lumen; and
   a staple disposed in an open position in the working lumen, the staple comprising a first tine and a second tine connected by a bridge portion, the staple further comprising a shape memory material and being configured to transition from the open position to a closed position at or above a transformation temperature of the shape memory material, an end of the first tine is oriented toward a distal end of the shaft and disposed distal to an end of the second tine in the open position, the end of the second tine is bent toward the end of the first tine so that the ends of the first tine and the second tine are oriented toward the distal end of the shaft and the ends of the first and second tines are positioned proximal to the distal end of the shaft in the open position for delivery to a treatment site.

2. The medical device according to claim 1, wherein at least one of the first tine and the second tine extend generally along a line of the bridge portion in the open position.

3. The medical device according to claim 1, wherein the staple is disposed in the closed position after delivery to a body tissue.

4. The medical device according to claim 3, wherein the end of the first tine and the end of the second tine are bent toward each other in the closed position, thereby enabling closure of an incision.

5. The medical device according to claim 1, further comprising a control mechanism extending through the working lumen of the elongate shaft to control delivery of the staple.

6. The medical device according to claim 1, wherein the transformation temperature of the shape memory material is in the range of from about 32° C. to about 40° C.

7. The medical device of claim 1, wherein the shape memory material is a shape memory alloy.

8. The medical device of claim 7, wherein the shape memory alloy comprises nickel and titanium.

9. The medical device according to claim 1, wherein the elongate shaft further comprises a proximal portion and a distal portion, and a slot disposed along a wall of the distal portion, the slot being configured to allow a portion of the staple to pass therethrough.

10. The medical device according to claim 9, wherein the first tine is extendable through the slot.

11. A medical device, comprising:
   a staple formed from a shape memory material and having an open position and a closed position;
   an elongate shaft having a working lumen extending at least partially therethrough and an opening at a distal end of the shaft, the working lumen extending along a longitudinal axis of the shaft and the working lumen being sized and shaped for receiving the staple in the open position so that a first and a second tine of the staple are proximal to the distal end of the shaft; and a control member extending along at least a portion of the lumen, the control member comprising a securing member at a distal portion of the control member to releasably secure the staple to the control member during delivery, the securing member being adapted for delivery of the first tine of the staple to a body tissue while retaining the second tine external to the body tissue during insertion of the first tine, wherein the staple assumes the closed position when disposed in the body tissue.

12. The medical device according to claim 11, wherein the elongate shaft further comprises a axial slot in a distal portion a wall of the elongate shaft, the slot being configured to allow a portion of the staple to pass therethrough.

13. The medical device according to claim 11, wherein an end of the first tine is disposed distal of an end of the second tine when the staple is received in the lumen in the open position.

14. The medical device according to claim 11, wherein the shape memory material comprises a high temperature phase and a low temperature phase.

15. The medical device according to claim 14, wherein the staple comprises the low temperature phase of the shape memory material in the open position and the high temperature phase of the shape memory material in the closed position.

16. A medical device, comprising:
    a staple formed from a shape memory material and having an open position and a closed position; and
    an elongate shaft having a working lumen extending at least partially therethrough and an opening at a distal end of the shaft, the working lumen extending along a longitudinal axis of the shaft and the working lumen being sized and shaped for receiving the staple in the open position so that an end of a first tine and an end of a second tine of the staple are proximal to the distal end of the shaft, the shaft further comprising an axial slot in a wall of a distal portion of the elongate shaft, a first portion of the staple is movable relative to the shaft to pass from the working lumen through the slot so that the first portion of the staple is extendable away from the longitudinal axis of the working lumen and the end of the first tine is extendable through the axial slot and positionable external to the wall of the shaft and a second portion of the staple is retained in the working lumen.

17. The medical device of claim 16, further comprising a control member extending along at least a portion of the lumen, the control member being adapted for delivery of the first tine of the staple to a body tissue while retaining the second tine external to the body tissue during insertion of the first tine.

18. The medical device of claim 17, wherein the control member is adapted for delivery of the first tine of the staple to a body tissue while retaining the second tine external to the body tissue during insertion of the first tine.

19. The medical device of claim 16, wherein the axial slot is connected to the opening.

20. The medical device of claim 16, wherein the end of the first tine is disposed distal of the end of the second tine when the staple is received in the lumen in the open position.

* * * * *